United States Patent [19]

Fauveau et al.

[11] Patent Number: 4,831,043
[45] Date of Patent: May 16, 1989

[54] DOPAMINERGIC BENZIMIDAZOL-2-ONES

[75] Inventors: Patrick Fauveau, Livry-Gargan; Lucien Nedelec, Le Raincy; Constantin Agouridas, Paris; Gilles Hamon, Montrouge, all of France

[73] Assignee: Roussel Uclaf, Paris, France

[21] Appl. No.: 155,303

[22] Filed: Feb. 12, 1988

[30] Foreign Application Priority Data

Feb. 13, 1987 [FR] France ................... 87 01836

[51] Int. Cl.$^4$ .................. A61K 31/44; C07D 401/10
[52] U.S. Cl. ................................ 514/322; 546/199
[58] Field of Search .................. 546/199; 514/322

[56] References Cited

U.S. PATENT DOCUMENTS 4,458,076  7/1984  Strupczewski ................ 546/199
4,680,296  7/1987  Manoury et al. ............ 546/199 X Primary Examiner—Ricahrd A. Schwartz
Attorney, Agent, or Firm—Bierman & Muserlian

[57] ABSTRACT

Novel benzimidazol-2-ones of the formula

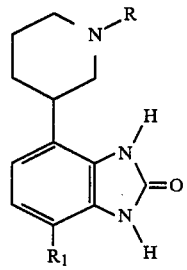

wherein R is selected from the group consisting of hydrogen, alkyl of 1 to 5 carbon atoms, cycloalkylalkyl of 4 to 7 carbon atoms, alkenyl and alkynyl of 3 to 5 carbon atoms with the multiple bond not between the carbons α- and β- to the nitrogen and aralkyl of 7 to 12 carbon atoms optionally substituted with at least one member of the group consisting of halogen and alkyl and alkoxy of 1 to 5 carbon atoms and $R_1$ is selected from the group consisting of hydrogen, —OH, alkoxy of 1 to 5 carbon atoms, phenoxy and phenylalkoxy of 7 to 9 carbon atoms and their non-toxic, pharmaceutically acceptable acid addition salts having dopaminergic, antiulcerous, and antihypertensive and vasodilatatory activity.

15 Claims, No Drawings

DOPAMINERGIC BENZIMIDAZOL-2-ONES

STATE OF THE ART

U.S. Pat. No. 4,332,808 describes derivatives of 4-(piperidin-3-yl)-1H-indole having marked dopaminergic stimulating activity on the central level.

OBJECTS OF THE INVENTION

It is an object of the invention to provide the novel products of formula I and their non-toxic, pharmaceutically acceptable acid addition salts and their preparation.

It is another object of the invention to provide novel pharmacological compositions and a novel method of inducing pharmacological activity in warm-blooded animals.

These and other objects and advantages of the invention will become obvious from the following detailed description.

THE INVENTION

The novel compounds of the invention are selected from the group consisting of benzimidazol-2-ones of the formula

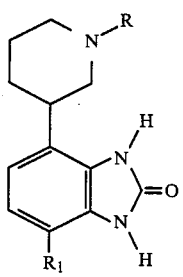

wherein R is selected from the group consisting of hydrogen, alkyl of 1 to 5 carbon atoms, cycloalkylalkyl of 4 to 7 carbon atoms, alkenyl and alkynyl of 3 to 5 carbon atoms with the multiple bond not between the carbon α- and β- to the nitrogen and aralkyl of 7 to 12 carbon atoms optionally substituted with at least one member of the group consisting of halogen and alkyl and alkoxy of 1 to 5 carbon atoms and $R_1$ is selected from the group consisting of hydrogen, —OH, alkoxy of 1 to 5 carbon atoms, phenoxy and phenylalkoxy of 7 to 9 carbon atoms and their non-toxic, pharmaceutically acceptable acid addition salts.

Examples of alkyl of 1 to 5 carbon atoms are methyl, ethyl, isopropyl and n-propyl and examples of cycloalkyalkyl of 4 to 7 carbon atoms are cyclopropylmethyl and cyclobutylmethyl. Examples of aralkyl of 7 to 12 carbon atoms are benzyl, phenethyl and naphthylmethyl which may be substituted on the aryl by one or more substituents such as alkoxy such as methoxy, ethoxy, isopropoxy or n-propoxy or halogen such as bromine and chlorine. Examples of alkenyl and alkynyl of 3 to 5 carbon atoms are allyl and propargyl and examples of phenylalkoxy of 7 to 9 carbon atoms are benzyloxy and phenethoxy.

The addition salts with mineral or organic acids can be, for example, the salts formed with the following acids: hydrochloric acid, hydrobromic acid, nitric acid, sulfuric acid, phosphoric acid, acetic acid, formic acid, propionic acid, benzoic acid, maleic acid, fumaric acid, succinic acid, tartaric acid, citric acid, oxalic acid, gly- oxylic acid, aspartic acid, alkanesulfonic acids and such as methane sulfonic acid, and ethane sulfonic acid, arysulfonic acids such as benzene and p-toluene-sulfonic acid and aryl carboxylic acids such as benzoic acid.

Among the preferred compounds of formula I are those wherein $R_1$ is hydrogen and those wherein R is hydrogen or alkyl of 1 to 5 carbon atoms. Specific preferred compounds of formula I are 1,3-dihydro-4(1-propyl-3-piperidinyl)-2H-benzimidazol-2-one and 1,3-dihydro-4-hydroxy-7-(1-propyl-3-piperidinyl)-2H-benzimidazol-2-one and their non-toxic, pharmaceutically acceptable acid addition salts.

The novel process of the invention for the preparation of compounds of formula I wherein $R_1$ is hydrogen comprises reacting a compound of the formula

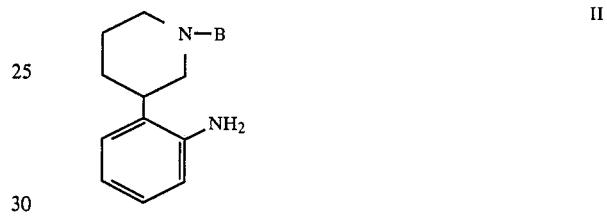

wherein B is a reversible blocking group for a secondary amine with an alkyl haloformate of the formula

wherein Hal is chlorine, bromine or iodine and Alk is alkyl of 1 to 5 carbon atoms to obtain a compound of the formula

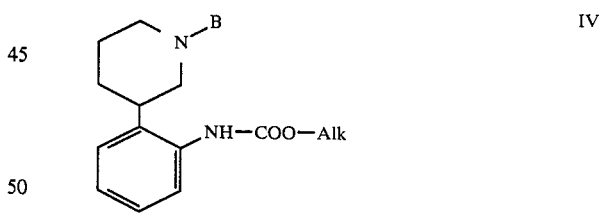

which is subjected to nitration to obtain a compound of the formula

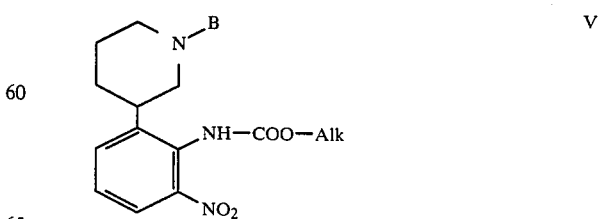

either reducing the nitro group to obtain a compound of the formula

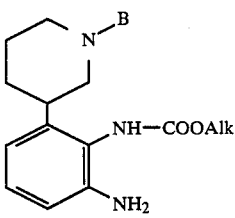

or reacting the compound of formulae V or VI with an agent to remove B to obtain a compound of the formula

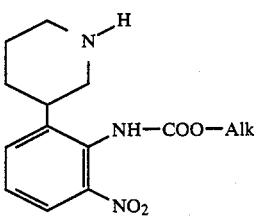

or

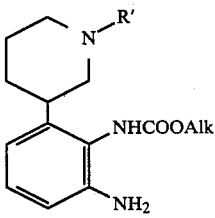

reacting the latter with a compound capable of providing R' wherein R' is R other than hydrogen to obtain a compound of the formula

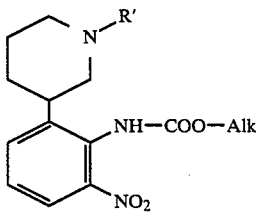

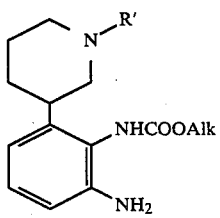

then reducing the nitro of the compounds of formula V' and V'" to obtain the compounds of VI' and VI" and cyclizing the latter by hydrolysis to obtain a compound of the formula

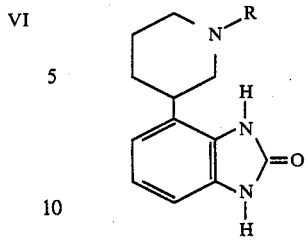

wherein R has the above definition and optionally salifying the latter.

The compounds of formula VI may also be cyclized and then the secondary amine of the piperidine may be unblocked to obtain a compound of formula I$_A$ where R is hydrogen which may be reacted to obtain other compounds of formula I when R is other than hydrogen.

The novel process of the invention for the preparation of compounds of formula I wherein R is other than hydrogen comprises reacting a compound of the formula

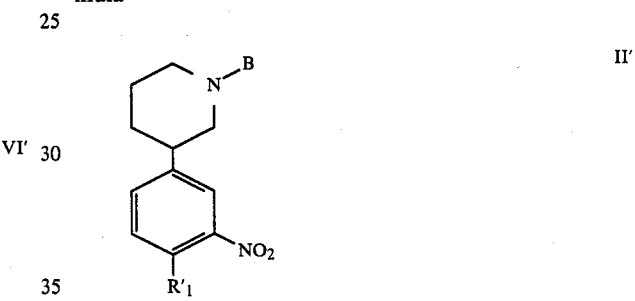

wherein B has the above definition and R$_1$ is R$_1$ other than hydrogen or —OH with phosgene or a phosgene precursor to obtain a compound of the formula

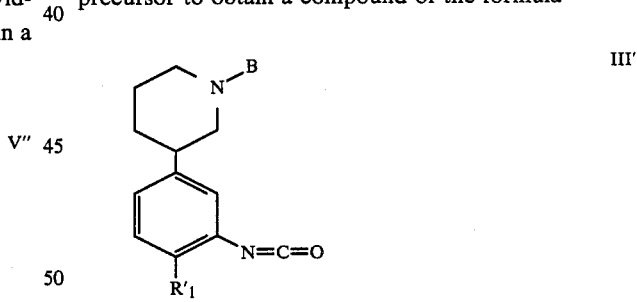

reacting the latter with O-benzylhydroxylamine to obtain a compound of the formula

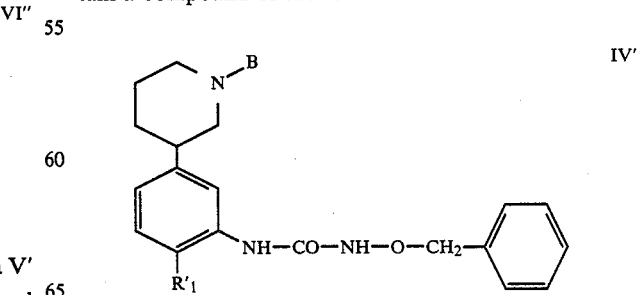

cyclizing the latter to obtain a compound of the formula

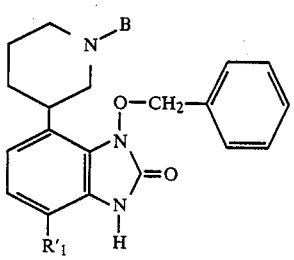

either unblocking the amine groups to obtain a compound of the formula

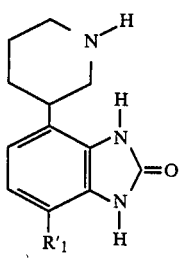

I'$_A$ which may be salified or selectively unblocking the piperidine amine to obtain a compound of the formula

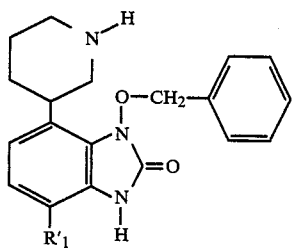

VIII reacting the latter with an agent to provide R' having the above definition to obtain a compound of the formula

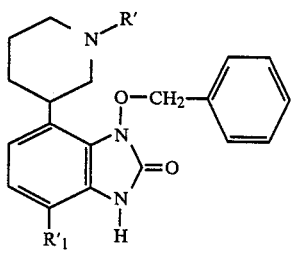

IX subjecting the latter to catalytic hydrogenation to obtain a compound of the formula

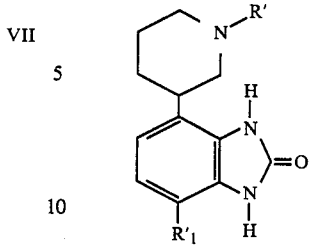

I'$_B$ and optionally salifying the latter or reacting a compound of formula I$_A$ or I$_B$ with an agent to unblock the hydroxy to obtain a compound of the formula

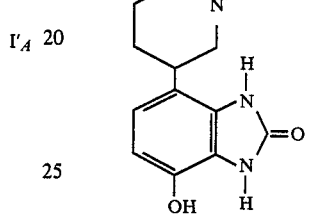

I'$_C$ which may be salified or successively unblocking the imidazole amine, the piperidine amine and finally the hydroxyl to obtain the compound of formula VII.

B is preferably trifluoroacetate and the reaction of the compounds of formulae II and III is preferably effected in the presence of a base such as pyridine or triethylamine in a chlorinated solvent such as methylene chloride. The nitration of the compound of formula IV is preferably carried out with nitronium tetrafluoroborate in a solvent such as acetonitrile but other nitration agents can also be used such as nitric acid in acetic anhydride or sulfuric acid or even a mixture of fuming nitric acid with trifluoroacetic acid.

The reduction of the nitro group of the compounds of formulae V, V' and V''' is preferably carried out by catalytic hydrogenation using a catalyst such as Raney nickel or preferably palladium on carbon or even a reduced metal such as iron or tin. The agent to unblock the amine of the piperidine ring, in the case of the trifluoroacetyl radical, is preferably a mineral base such as the hydroxide of sodium or potassium, or an alkali metal carbonate such as sodium or potassium carbonate. The agent able to graft on R' is preferably a halide of the formula Hal-R''  X in which R'' has the significance of R with the exception of hydrogen and methyl.

The halide of formula X can be chloride or bromide, but is preferably iodide and reacts advantageously with the secondary amines of formula V' in the presence of an acid fixing agent such as an alkali metal carbonate such as potassium carbonate in a solvent such as dimethylformamide. To fix R' on the compounds of formulae V' and VI', the operation can also be done by reacting the compounds of formulae V' and VI' with an aldehyde or a ketone of the formula

in which $R_2$ and $R_3$ are such that

is alkyl of 1 to 5 carbon atoms in the presence of a reducing agent such as alkali metal borohydride, cyanoborohydride or catalytic hydrogenation. In this way if the compound of formula XI is formaldehyde or acetaldehyde, there are obtained respectively methyl and ethyl for R'.

The cyclization of the compounds of formulae VI, VI' and VI" is preferably carried out by alkaline hydrolysis using as the base an alkali metal hydroxide such as sodium hydroxide or preferably potassium hydroxide. When a precursor of phosgene is used to prepare a compound of formula I in which $R_1$ is hydroxyl or alkoxy, trichloromethyl chloroformate is used. The reaction of the compound of formula III' with III' with O-benzylhydroxyl amine, preferably salified in the form of the hydrochloride, is in these preferential conditions, carried out at ambient temperature.

The unblocking of the amine of the imidazol is preferably carried out by catalytic hydrogenation with platinium-rhodium or particularly with Raney's nickel. The unblocking of the amine of the piperidine and the other reaction conditions have been described above.

The starting compounds of formula II may be prepared by reducing a compound of the formula

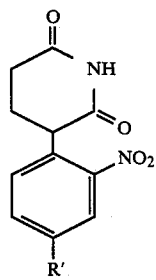

in which R' has the above definition to obtain a compound of the formula

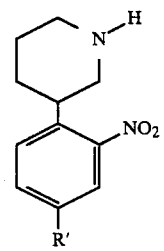

in which R' has the above definition of which the secondary amine is protected, to obtain a compound of the formula

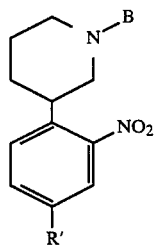

in which B and R' have the above definition and reducing the latter to obtain a compound of formula II.

The reduction of the derivative of formula XII is preferably carried out with diborane prepared in situ, for example, with sodium borohydride and boron trifluoride etherate. The agent able to block the amine of formula XIII reversibly is trifluoroacetic anhydride, preferably in the presence of a base when B is trifluoroacetyl. The reduction of the compound of formula XIV is preferably carried out as indicated above for the compounds of formulae V, V' and V'''.

The compounds of formula XII are known, for example, Synthesis 1061 (1984), or can be prepared, for example, by cyclizing a compound of the formula

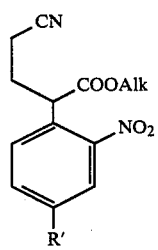

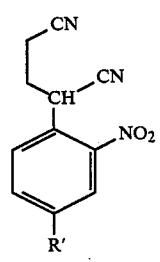

in which Alk and R' have the above definition with sulfuric acid in acetic acid.

The products of formula XVI can be prepared, for example, by reaction of a derivative of the formula

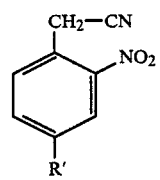

in which R' has the above definition with acrylonitrile in the presence of N-benzyltrimethyl ammonium hydroxide.

The compounds of formula I have a basic character and the acid addition salts thereof can advantageously be prepared by reacting a mineral or organic acid with the said derivative of formula I in about stoichiometric proportions. The salts can be prepared without isolating the corresponding bases.

The pharmacological compositions of the invention are comprised of an effective amount of at least one compound of formula I and its non-toxic, pharmaceutically acceptable acid addition salts and an inert pharmaceutical carrier or excipient. The compositions may be in the form of tablets, dragees, capsules, suppositories or injectable solutions or suspensions.

The compositions have dopaminergic properties and antihypertensive and vasodilation, and anti-ulcerous properties. They are useful in the treatment of cerebral vascular mishaps, peripheral circulation disorders such as retinal or nephritic, in glaucoma or in arterial diseases of the lower limbs. They can also be used in the treatment of cardiac insufficiencies of various etiologies and in the treatment of gastric or duodenal ulcers.

Examples of suitable execipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The novel method of the invention for introducing pharmaco logical activity in warm-blooded animals, including humans, comprises administering to warm-blooded animals an effective amount of at least one compound of formula I and its non-toxic, pharmaceutically acceptable acid addition salts. The compounds may be administered orally, rectally or parenterally. The usual daily dose is depending on the condition treated, the specific compound and method of administration. A daily dose of 0.15 to 3 mg/kg is effective for the treatment of cardiac insufficiency.

The novel intermediates of the invention are the compounds of the formula

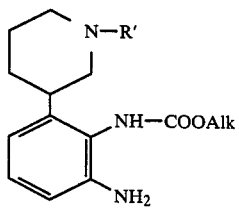

VI''

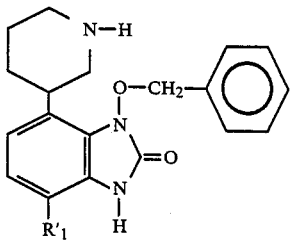

VIII in which R, $R_1$ and Alk have the above definition.

In the following examples there are described several preferred embodiments to illustrate the invention. However, it should be understood that the invention is not intended to be limited to the specific embodiments.

EXAMPLE 1

1,3-dihydro-4-(3-piperidinyl)-2H-benzimidazol-2-one

STEP A:

3-(2-nitrophenyl-1-(trifluoroacetyl)-piperidine

With stirring under an inert atmosphere, 24 g of 95% sodium borohydride were added to a solution of 25.9 g of 3-(2-nitrophenyl)-piperidine-2,6-dione (described in Synthesis 1061, (1984) in 600 ml of tetrahydrofuran and cooled to 0 C. 97 ml of boron trifluoride etherate were added dropwise over 45 minutes, and the mixture was stirred for 16 hours at ambient temperature, then cooled to 0° C. The excess of diborane was eliminated by the slow addition of 150 ml of ethanol and 200 ml of 2N hydrochloric acid were added. The tetrahydrofuran was eliminated under reduced pressure and the residue was taken up in methylene chloride, decanted, alkalized with concentrated ammonia, and then extracted with methylene chloride. The extracts were washed with water, dried, taken to dryness under reduced pressure to obtain 21 g of the reduced product.

A partial solution of the above product in 500 ml of methylene chloride was cooled to 0° C. and then over 25 minutes, 28.9 ml of trifluoroacetic anhydride were added dropwise. After stirring for 90 minutes at ambient temperature, then cooling to 0° C., 100 ml of water were added. Sodium bicarbonate was added in small fractions until neutrality was achieved, followed by decanting, drying, evaporating to dryness under reduced pressure and inducing crystallization by the addition of isopropyl ether, 23.7 g of the expected product melting at about 70° C. after crystallization from isopropyl ether were obtained.

STEP B:

3-(2-aminophenyl)-1-(trifluoroacetyl)-piperidine 3.86 g of the product of Step A were hydrogenated for 3 hours in 150 ml of ethanol in the presence of 0.96 g of palladium at 10% on carbon and the mixture was then filtered. The product was washed with ethanol, taken to dryness under reduced pressure and triturated in ethyl ether. After separating and drying, 3.2 g of 3-(2-aminophenyl)-1-(trifluoroacetyl)-piperidine melting at about 138° C. after crystallization from isopropyl ether were obtained.

STEP C:

Ethyl-[2-[1-(trifluoroacetyl)-3-piperidinyl]-phenyl]-carbamate 2.2 g of 3-(2-aminophenyl)-1-(trifluoroacetyl)-piperidine in 100 ml of methylene chloride, 3 ml of pyridine and 1 ml of ethyl chloroformate were stirred for one hour, washed with 2N hydrochloric acid and then with water, dried, taken to dryness under reduced pressure to obtain 2.8 g of an oil which was used as is for the following step.

STEP D:

Ethyl-[2-nitro-6-[1-trifluoroacetyl-3-piperidinyl]-phenyl]-carbamate

A solution of 18 g of product of Step C in 180 ml of acetonitrile was cooled to −30° C. and then with stirring and under an inert atmosphere, 7.73 g of nitronium tetrafluoroborate were added in small fractions. After stirring for one hour and returning to ambient temperature, the reaction mixture was poured on to ice and extracted with methylene chloride. The extracts were washed with water, dried, taken to dryness under reduced pressure and purified by chromatography on silica (eluent: cyclohexane-ethyl acetate 7-3) to obtain 10.8 g of the expected product (RF=0.2) melting about 124° C. after crystallization from a mixture of isopropyl ether and methylene chloride (1-1).

STEP E:
Ethyl-[2-amino-6-[1-(trifluoroacetyl)-3-piperidinyl]-phenyl]-carbamate 12 g of the product of Step D were hydrogenated for 3 hours in 400 ml of ethanol in the presence of 3 g of palladium at 10% on carbon. After filtering, washing with ethanol and evaporating to dryness under reduced pressure, 10.8 g of ethyl-[2-amino-6-[1-(trifluoroacetyl)-3-piperidinyl]-phenyl]-carbamate melting at about 90° C. after crystallization from isopropyl ether were obtained.

STEP F:
1,3-dihydro-4-(3-piperidinyl)-2H-benzimidazol-2-one 4 g of the product of Step E in 80 ml of methanol, 16 ml of water and 16 ml of potassium hydroxide were taken to 80° C. for 4 hours with stirring under an inert atmosphere. After evaporating the methanol under reduced pressure, adding 30 ml of water, adjusting the pH to 6-8 by acetic acid and taking to dryness under reduced pressure, the residue was purified by chromatography on silica, (eluent: methylene chloride-methanol-triethylamine (6-3-1) to obtain 2.15 g of crude product. The latter was triturated in ethyl ether, separated, dried and crystallized from ethanol to obtain 1.23 g of 1,3-dihydro-4-(3-piperidinyl)-2H-benzimidazol-2-one melting at about 260° C.

U V Spectrum, (ethanol). Max. 229 nm $E^1_1=276=6000$, Max. 280 nm $E^1_1=224$, Max. 283 nm $E^1_1=278=4950$.

EXAMPLE 2
1,3-dihydro-4-(1-propyl-3-piperidinyl)-2H-benzimidazol-2-one and its acetate 4.7 g of the product of Step E of Example 1 in 80 ml of methanol and 20 ml of water were stirred for one hour with 8 g of sodium carbonate and then were extracted with methylene chloride. The extracts were washed with water, dried and taken to dryness under reduced pressure to obtain 3.2 g of the expected product.

With stirring under an inert atmosphere, 0.74 ml of propionaldehyde were added to a solution of 2.45 g of the above product and 635 mg of sodium cyanoborohydride in 70 ml of methanol. After stirring for 16 hours, the reaction medium was poured into ice water and extracted with methylene chloride. The extracts were dried, taken to dryness under reduced pressure and purified by chromatography on silica (eluent: methylene chloride-methanol, 98-2) to obtain 1.95 g of the expected product.

U V Spectrum, (ethanol). Max. 237 nm $E^1_1=256=7800$, Max. 289 nm $E^1_1=83=2550$.

STEP B:
1,3-dihydro-4-(1-propyl-3-piperidinyl)-2H-benzimidazol-2-one and its acetate 1.4 g of product of Step A in 30 ml of methanol, 6 ml of water and 6 ml of potassium hydroxide were heated to 80° C. for five hours with stirring and the methanol was then evaporated off. 6 ml of water were added and the pH was adjusted to 6.4 with hydrochloric acid. After taking to dryness under reduced pressure and purifying by chromatography on silica (eluent: methylene chloride-methanol, 98-2), 1.02 g of the expected product were obtained in the form of its base.

2.5 ml of acetic acid were added to a solution of 0.92 g of the above base in 10 ml of methylene chloride and after taking to dryness under reduced pressure and taking up the residue with 15 ml of water, filtering and lyophilizing, 850 mg of the expected acetate were obtained.

U V Spectrum, (ethanol). Max. 230 nm $E^1_1=245=7800$, Max. 283 nm $E^1_1=201=6400$.

U V Spectrum, (ethanol-0.1N NaOH) Max. 246 nm $E^1_1=191=6100$, Max. 287 nm $E^1_1=232=7400$.

EXAMPLE 3
1,3-dihydro-4-(1-methyl-3-piperidinyl)-2H-benzimidazol-2-one and its hydrochloride Using the procedure of Example 2, the alkylation was effected with formaldehyde to obtain the expected product with a melting point greater than 250° C. (hydrochloride).

| NMR Spectrum (DMSO) 60 MHz (hydrochloride). | |
|---|---|
| H of the N—methyl | 2.2 ppm |
| H aromatics | 6.9 ppm |
| other protons of the ring | 1.5 to 2.9 ppm |
| H mobiles | 10.6 to 10.8 ppm. |

EXAMPLE 4
1,3-dihydro-4-hydroxy-7-(3-piperidinyl)-2H-benzimidazol-2-one hydrobromide

STEP A:
3-(3-isocyanato-4-methoxyphenyl)-1-trifluoroacetyl-piperidine 6.04 g of 3-(3-amino-4-methoxyphenyl)-1-trifluoroacetyl piperidine in 120 ml of dioxane and 2.9 ml of trichloromethyl chloroformate were mixed together and stirred for 4 hours at 80° C. Then, the mixture was evaporated to dryness under reduced pressure. The residue was chromatographed on silica and eluted with a mixture of cyclohexane and ethyl acetate (7-3) to obtain 6.4 g of crude product which was used as is for the following step.

STEP B:
3-(3-[[[(phenylmethoxy)-amino]-carbonyl]-amino]-4-methoxyphenyl)-1-trifluroacetyl piperidine 1.68 g of O-benzyl-hydroxylamine hydrochloride suspended in 30 ml of methylene chloride were added to 1.52 ml of triethylamine and then 3.2 g of the product of Step A in 10 ml of methylene chloride were added dropwise with stirring for 2 hours, followed by evaporating to dryness under reduced pressure. The residue was chromatographed on silica, (eluent: methylene chloride-ethyl acetate 96-4) to obtain 3.75 g of the expected product melting at 134° C. after crystallization from a 1-1 mixture of methylene chloride and isopropyl ether.

STEP C:
1,3-dihydro-4-methoxy-1-(phenylmethoxy)-7-[1-(trifluoroacetyl-3-piperidinyl]-2H-benzimidazol-2-one 3.7 g of the product of Step B in 90 ml of methylene chloride were cooled to 0° C. and then a solution of lead tetracetate in 50 ml of anhydrous methylene chloride was added dropwise. After stirring for one hour, the precipitate formed was filtered off and the filtrate was washed with water, dried, and evaporated to dryness under reduced pressure. The residue was chromatography on silica and eluted with a mixture of methylene chloride and methanol (95-5) to obtain 2.88 g of the expected product melting at 192° C. after crystallization from a 20-15 mixture of isopropyl ether and methylene chloride.

STEP D:
1,3-dihydro-4-methoxy-7-[1-(trifluoroacetyl)-3-piperidinyl]-2H-benzimidazol-2-one 2.1 g of the product of Step C in 70 ml of ethanol was hydrogenated for 12 hours with 2 g of Raney's nickel and after filtering, the filtrate was taken to dryness under reduced pressure. The residue was crystallized from a 15-5 mixture of methylene chloride and isopropyl ether to obtan 0.935 g of the expected product melting at about 260° C.

U.V. Spectrum, (in EtOH). Max. 214 nm $E^1_1=1981=68,000$, Inflexion 237 nm $E^1_1=361$, Inflexion 246 nm $E^1_1=227$.

Inflexion 248 nm $E^1_1=189$, Max. 270 nm $E^1_1=63=2,150$, Max. 279 nm $E^1_1=46=1,600$.

STEP E:
1,3-dihydro-4-hydroxy-7-(3-piperidinyl)-2H-benzimidazol-2-one hydrobromide 1.1 g of the product of Step D were stirred for one hour in 15 ml of methanol, 5 ml of water and 680 mg of sodium carbonate. After adding a few ml of water, extraction was done with methylene chloride and the extracts were dried and taken to dryness under reduced pressure. The residue was taken up with 50 ml of methylene chloride, cooled to −30° C., and dropwise, 9.6 ml of an M solution of boron tribromide in methylene chloride were added. The mixture was stirred for 3 hours and then cooled to 0° C. and 30 ml of methanol were added. After 15 minutes at ambient temperature, and taking to dryness under reduced pressure, the residue was taken up in methylene chloride and separated to obtain 840 mg of the expected product melting at greater than 250° C. After recrystallizing the hydrobromide in methanol, 600 mg of the expected product were obtained.

U.V. Spectrum, (in EtOH). Max. 212 nm $E^1_1=1924=60,500$, Inflexion 233 nm $E^1_1=311$, Max. 270 nm $E^1_1=51=1,600$, Inflexion 280 nm $E^1_1=30$.

U.V. Spectrum, (in EtOH+0.1N NaOH) Max. 250 nm $E^1_1=341=10,700$, Inflexion 288 nm $E^1_1=30$.

| NMR Spectrum (DMSO) | |
|---|---|
| 1.8 ppm | H of the CH$_2$ in beta and alpha of N |
| 2.77–3.55 ppm | H of the CH$_2$ N$^\oplus$ and CH$\Phi$· |
| 6.33–6.42 ppm | } H, aromatics |
| 6.52–6.61 ppm | |
| 8.14–8.84, 8.98 ppm | } H, mobiles. |
| 10.4–10.62 ppm | |

EXAMPLE 5
1,3-dihydro-4-hydroxy-7-(1-propyl-3-piperidinyl)-2H-benzimidazol-2-one hydrobromide

STEP A
1,3-dihydro-4-methoxy-1-(phenylmethoxy)-7-(3-piperidinyl)-2H-benzimidazol-2-one Over 5 minutes, 33 ml of 2N sodium hydroxide were added to a cooled solution of 5 g of the product of Step C of Example 4 in 500 ml of ethanol and the mixture was stirred for 1 hour at ambient temperature, then neutralized to pH 6 with N hydrochloric acid. The mixture was extracted with a mixture of methylene chlorideand methanol (9-1) and the extracts were dried and the solvents were eliminated under reduced pressure to obtain 4.5 g of the expected product.

STEP B:
1,3-dihydro-4-methoxy-1-(phenylmethoxy)-7-(1-propyl-3-piperidinyl)-2H-benzimidazol-2-one To a solution of 4.39 g of the product of Step A in 150 ml of methanol, there was added 1.076 ml of propionaldehyde and 0.937 g of sodium cyanoborohydride with stirring for 4 hours at ambient temperature. 50 ml of water were added, following by extracting with methylene chloride. The extracts were dried and the solvents were eliminated under reduced pressure to obtain 2.2 g of the expected product after chromatography on silica (eluent: methylene chloride-methanol 9-1)

IR Spectrum (CHCl$_3$): =C—NH: 3461 cm$^{-1}$, Bohlman's bands,

1718 cm$^{-1}$, aromatic: 1640–1525–1500 cm$^{-1}$.

STEP C:
1,3-dihydro-4-methoxy-7-(1-propyl-3-piperidinyl)-2H-benzimidazol-2-one 2.2 g of the product of Step B were hydrogenated for two and a quarter hours in 30 ml of ethanol inthe presence of 3.5 g of Raney's nickel. After filtering, the filrate was taken to dryness under reduced pressure to obtain 1.5 g of crude product which was chromatographed on silica (eluent: methylene chloride-methanol 9-1) to obtain 1.1 g of pure product.

IR Spectrum (CHCl$_3$): —NH: 3470 cm$^{-1}$ (+associated),

1698 cm$^{-1}$, aromatic: 1642–1526–1512 cm$^{-1}$.

STEP D:
1,3-dihydro-4-hydroxy-7-(1-propyl-3-piperidinyl)-2H-benzimidazol-2-one hydrobromide 1 g of the product of Step C in 100 ml of methylene chloride was cooled to 0°/+5° C. and over 5 minutes, 24 ml of an M solution of boron tribromide in methylene chloride were added dropwise. After stirring for 4 hours at ambient temperature and then cooling to 0° C., 50 ml of methanol were added slowly and the solvents were eliminated under reduced pressure. The residue was taken up in methanol and filtered to obtain 1.05 g of the expected product. 0.75 g of this product were purified by chromatography on silica (eluent: methylene chloride-methanol-triethylamine 8-1-1) to obtain 0.36 g of pure product which was crystallized from methanol.

UV Spectrum in EtOH. max. 213 nm $E^1_1=1649=58,800$, inflexion 233 nm $E^1_1=274$, max, 271 nm $E^1_1=44=1,550$, inflexion 279 nm $E^1_1=25$.

EXAMPLE 6

1,3-dihydro-4-hydroxy-7-(1-methyl-3-piperidinyl)-2H-benzimidazol-3-one hydrobromide

STEP A:

1,3-dihydro-4-methoxy-7-(1-methyl-3-piperidinyl)-1-(phenylmethoxy)-2H-benzimidazol-3-one Using the procedure of Step B of Example 5, 4.4 g of the product of Step A of Example 5 and 1.9 ml of formaldehyde were reacted to obtain 3.6 g of crude product which was purified by double extraction (2N HCl then methylene chloride) to obtain 1.7 g of the expected product.

IR Spectrum (CHCl₃): =C—NH: 3461 cm⁻¹, Bohlman's bands

1719 cm⁻¹, aromatic: 1640–1525 cm⁻¹.

STEP B:

1,3-dihydro-4-methoxy-7-(1-methyl-3-piperidinyl)-2H-benzimidazol-2-one

Using the procedure of Example 5, Step C, 1.6 g of the product of Step A in the presence of 2 g of Raney's nickel were reacted to obtain 1.1 g of product which was dissolved in a mixture of ethanol and methylene chloride, concentrated and crystallized by addition of ether to obtain the expected product melting greater than 250° C.

IR Spectrum: —NH: 3470 cm⁻¹+associated absorption OH/NH, C=O: 1697 cm⁻¹, aromatic: 1640–1525–1512 cm⁻¹.

STEP C:

1,3-dihydro-4-hydroxy-7-(1-methyl-3-piperidinyl)-2H-benzimidazol-3-one hydrobromide Using the procedure of Step D of Example 5, 0.7 g of the product of Step B and 20 ml of boron tribromide were reacted to obtain 0.630 g of the expected product which was purified by crystallizing from methanol.

UV Spectrum in EtOH. max. 212 nm $E^1_1=1796$, $\epsilon=58,900$, inflexion 232 nm $E^1_1=299$, inflexion 244 nm $E^1_1=174$, max. 271 nm $E^1_1=48$, $\epsilon=1,600$, inflexion 279 nm $E^1_1=28$.

EXAMPLE 7

Tablets have been prepared containing 10 mg of 1,3-dihydro-4-(3-piperidinyl)-2H-benzimidazol-2-one and sufficient excipient of lactose, starch, talc and magnesium stearate for a final tablet weight of 100 mg.

EXAMPLE 8

Tablets have been prepared containing 10 mg of acetate of 1,3-dihydro-4-(1-propyl-3-piperidinyl)-2H-benzimidazol-2-one and sufficient excipient of lactose, starch, talc and magnesium stearate for a final weight of 100 mg.

PHARMACOLOGICAL STUDY (1) Rotational behaviour after unilateral lesion of the nigrostriated bundle by 6-hydroxydopamine.

Male rats of about 220 g weight were injured in the nigrostriated dopaminergic bundle by a modified Ungerstedt's method [Acta. physiol. Scand. 1971, 82 suppl. 367–69 93] by unilateral injection of 9.2 g of 6-hydroxydopamine hydrochloride in solution in 4 microliters of physiological solution containing 0.4 mg/ml of ascorbic acid. The products studied were administered intraperitoneally and the treated animals were placed individually in a rotameter which enabled the counting of the number of rotations made by each animal in the direction opposite to that of the injured side.

Under the conditions of the test, the following results were obtained: the product of Example 6 was inactive at a dose of 5 mg/kg and only induced a rotational behavior starting with a dose of 10 mg/kg. Taking account of the very great sensitivity of this model, the central dopaminergic agonist activity of this compound was therefore weak.

(2) Test of revealing a direct vasodilatation activity (or post-synaptic relaxing vascular activity).

Rats of Sprague-Dawley strain with a weight of 320–350 g were anesthetized with pentobarbital (50 mg/kg by interperitoneal injection). After insertion of a carotid catheter to measure the arterial pressure and a jugular catheter for the injection of the compounds to be stidied as well as the eventual antagonists, the animals were demedulated by a steel rod which was introduced by the right orbital hole and passed down the whole length of the spinal marrow. The animals were then placed immediately under assisted respiration and some minutes after stabilization of arterial pressure, the animals received an intravenous perfusion of angiotensine II of 0.50 micrograms/kg per minute to increase their average pressure by about 100 mm of mercury. After obtaining a plateau, the test compound was injected intravenously every 2 minutes and in cumulative doses. The percentages of fall of the average arterial pressure so obtained enabled a curve of dose-response to be drawn reflecting the vasodilatation activity of the molecule studied. Previous treatment of the animals by different antagonists enabled the mechanism of action of this molecule to be distinguished. The products were tested between 0.001 and 1 mg/kg and domperidone and propanolol were used as antagonists. It can be concluded that the product of Example 4 had a vasodilatation effect starting at a dose of 0.03 mg/kg.

(3) Study of the acute toxicity

The lethal doses LD$_O$ of the different compounds tested were evaluated after administration by oral route in mice. The maximum dose not causing any mortality in 8 days was called LD$_O$ and the following results were obtained:

| Product of example | LD$_O$ in mg/kg |
| --- | --- |
| 1 | greater than 400 |

-continued

| Product of example | LD₀ in mg/kg |
|---|---|
| 4 | greater than 400 |

(4) Affinity for the dopaminergic receptors

The striated bodies removed from the brains of 6 male rats weighing an average of 150 g were homogenized to the twentieth (weight/volume) in 0.32M sucrose. After centrifuging the homogenized mixture at 1,000 g for 10 minutes at 0° C. the supernatant was centrifuged at 30,000 g for 15 minutes at +4° C. The residue was taken up in 25 ml of Tris HCl 50 mM buffer, pH 7.7, and centrifuged at 30,000 g for 15 minutes at +4° C. The new residue was taken up in 50 ml of Krebs Tris HCl buffer pH 7.3, and the suspension was pre-incubated fo 10 minutes at 37° C. It was then incubated for 20 minutes on a water-bath at +37° C. in the presence of 3H spinoperidol alone, with an excess of haloperidol and with increasing concentrations of the product under test. The incubated suspensions were filtered on Whatman GF/C and the filters were washed three times with 5 ml of Tris HCl 50 mM buffer. The radioactivity of the filters was measured by liquid scintillation.

The non-specific fixation were determined in parallel by incubation of 3H spiroperidol in the presence of an excess of haloperidol and the following results were obtained. The result was expressed directly in 50% inhibiting concentrations, ($IC_{50}$: concentration of product studied, expressed in nM, necessary to displace 50% of the specific radio-activity fixed on the receptor studied).

| Product of example | $IC_{50}$ in (nM) |
|---|---|
| 1 | 172 |
| 4 | 300 |

(5) Study of the hypotensive activity on anesthetized "normotendu" rat.

Male Sprague-Dawley rats (CR) were anesthetized intraperitoneally with sodium pentobarbital (60 mg/Kg). A jugular vein was catheterized for injection of the product and a carotid artery was catheterized for registration of the arterial pressure. The product to be tested was dissolved in 10% of ethanol and then injected at a volume of 1 ml/kg. The pressure was noted at times of 5 minutes and 30 minutes after injection of the product. The following table indicates the variations of the arterial pressure after administration of the product tested expressed as a percentage of the initial control arterial pressure.

Results:

| Product of example | dose mg/kg | 5 min. after administration | 30 min. after administration |
|---|---|---|---|
| 5 | 10 | −23 | −21 |
|   | 1 | −19 | −19 |
| 4 | 0.1 |  | −17 |

Various modifications of the products and methods of the invention may be made without departing from the spirit or scope thereof and it is to be understood that the invention is to be limited only as defined in the appended claims.

What we claim is:

1. A compound selected from the group consisting of benzimidazol-2-ones of the formula

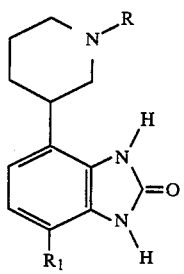

wherein R is selected from the group consisting of hydrogen, alkyl of 1 to 5 carbon atoms, cycloalkylalkyl of 4 to 7 carbon atoms, alkenyl and alkynyl of 3 to 5 carbon atoms with the multiple bond not between the carbons α- and β- to the nitrogen and aralkyl of 7 to 12 carbon atoms unsubstituted or substituted with at least one member of the group consisting of halogen and alkyl and alkoxy of 1 to 5 carbon atoms and $R_1$ is selected from the group consisting of hydrogen, —OH, alkoxy of 1 to 5 carbon atoms, phenoxy and phenylalkoxy of 7 to 9 carbon atoms and their non-toxic, pharmaceutically acceptable acid addition salts.

2. A compound of claim 1 wherein $R_1$ is hydrogen.

3. A compound of claim 2 wherein R is hydrogen or alkyl of 1 to 5 carbon atoms.

4. A compound of claim 1 selected from the group consisting of 1,3-dihydro-4-(1-propyl-3-piperidinyl)-2H-benzimidazol-2-one, and its non-toxic, pharmaceutically acceptable acid addition salts.

5. A compound of claim 1 selected from the group consisting of 1,3-dihydro-4-hydroxy-7-(1-propyl-3-piperidinyl)-2H-benzimidazol-2-one, and its non-toxic, pharmaceutically acceptable acid addition salts.

6. A dopaminergic composition comprising a dopaminergically effective amount of at least one compound of claim 1 and an inert pharmaceutical carrier.

7. A composition of claim 6 wherein $R_1$ is hydrogen.

8. A composition of claim 7 wherein R is hydrogen or alkyl of 1 to 5 carbon atoms.

9. A composition of claim 6 wherein the active compound is selected from the group consisting of 1,3-dihydro-4-(1-propyl-3-piperidinyl)-2H-benzimidazol-2-one, and its non-toxic, pharmaceutically acceptable acid addition salts.

10. A composition of claim 6 wherein the active compound is selected from the group consisting of 1,3-dihydro-4-hydroxy-7-(1-propyl-3-piperidinyl)-2H-benzimidazol-2-one, and its non-toxic, pharmaceutically acceptable acid addition salts.

11. A method of inducing dopaminergic activity in warm-blooded animals comprising administering to warm-blooded animals a dopaminergically effective amount of at least one compound of claim 1.

12. A method of claim 11 wherein $R_1$ is hydrogen.

13. A method of claim 12 wherein R is hydrogen or alkyl of 1 to 5 carbon atoms.

14. A method of claim 11 wherein the active compound is selected from the group consisting of 1,3-dihydro-4-(1-propyl-3-piperidinyl)-2H-benzimidazol-2-one, and its non-toxic, pharmaceutically acceptable acid addition salts.

15. A method of claim 11 wherein the active compound is selected from the group consisting of 1,3-dihydro-4-hydroxy-7-(1-propyl-3-piperidinyl)-2H-benzimidazol-2-one, and its non-toxic, pharmaceutically acceptable acid addition salts.

* * * * *